(12) United States Patent
Kelly

(10) Patent No.: US 9,629,738 B2
(45) Date of Patent: Apr. 25, 2017

(54) GUIDE WIRE WITH MULTI-LUMEN ACCESS THREADS

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 0 days.

(21) Appl. No.: 15/059,124

(22) Filed: Mar. 2, 2016

(65) Prior Publication Data

US 2016/0256302 A1 Sep. 8, 2016

Related U.S. Application Data

(60) Provisional application No. 62/127,257, filed on Mar. 2, 2015.

(51) Int. Cl.
*A61F 2/95* (2013.01)
*A61F 2/07* (2013.01)
(Continued)

(52) U.S. Cl.
CPC ............... *A61F 2/95* (2013.01); *A61F 2/07* (2013.01); *A61F 2/954* (2013.01);
(Continued)

(58) Field of Classification Search
CPC ...... A61F 2/06; A61F 2/07; A61F 2/95; A61F 2/954; A61F 2002/061; A61F 2002/065;
(Continued)

(56) References Cited

U.S. PATENT DOCUMENTS

| 5,824,055 A * | 10/1998 | Spiridigliozzi ......... A61F 2/966 606/195 |
| 6,447,530 B1 * | 9/2002 | Ostrovsky ................. A61F 2/01 606/108 |

(Continued)

FOREIGN PATENT DOCUMENTS

| EP | 2777606 A1 | 9/2014 |
| WO | 2005/009214 A2 | 2/2005 |
| WO | 2007/142962 A2 | 12/2007 |

OTHER PUBLICATIONS

International Search Report and Written Opinion for corresponding PCT application No. PCT/US2016/0250503, dated Aug. 9, 2016.

*Primary Examiner* — Sarah W Aleman
(74) *Attorney, Agent, or Firm* — McDonnell Boehnen Hulbert & Berghoff LLP

(57) ABSTRACT

The present disclosure provides an apparatus comprising (a) a guide wire having a first end and a second end, (b) an affixing harness coupled to the guide wire, the affixing harness having at least one projection extending towards the first end of the guide wire, (c) a plurality of alignment strings having a first end and a second end, where the first end of each of the plurality of alignment strings is removably coupled to the at least one projection of the affixing harness, and (d) an affixing shield removably coupled to at least one of the affixing harness and the guide wire, wherein the affixing shield is movably positioned over the at least one projection of the affixing harness.

29 Claims, 5 Drawing Sheets

(51) Int. Cl.
 *A61M 25/09* (2006.01)
 *A61F 2/954* (2013.01)
 *A61F 2/06* (2013.01)

(52) U.S. Cl.
 CPC . *A61M 25/09033* (2013.01); *A61F 2002/061* (2013.01); *A61F 2002/065* (2013.01); *A61F 2002/072* (2013.01); *A61F 2002/075* (2013.01); *A61F 2002/9505* (2013.01); *A61F 2002/9522* (2013.01); *A61M 2025/09175* (2013.01); *A61M 2025/09183* (2013.01)

(58) Field of Classification Search
 CPC ..... A61F 2002/9505; A61F 2002/9511; A61B 17/32056; A61B 2017/00349; A61B 2017/00358; A61M 25/09041; A61M 2025/0177; A61M 2025/09175; A61M 2025/090183
 See application file for complete search history.

(56) References Cited

U.S. PATENT DOCUMENTS

| | | | |
|---|---|---|---|
| 7,959,666 B2 * | 6/2011 | Salahieh | A61F 2/2418 623/1.26 |
| 2006/0155363 A1 | 7/2006 | Laduca et al. | |
| 2008/0262592 A1 * | 10/2008 | Jordan | A61F 2/95 623/1.11 |
| 2011/0270374 A1 * | 11/2011 | Orr | A61F 2/95 623/1.11 |
| 2014/0121754 A1 * | 5/2014 | Hadley | A61F 2/07 623/1.12 |

* cited by examiner

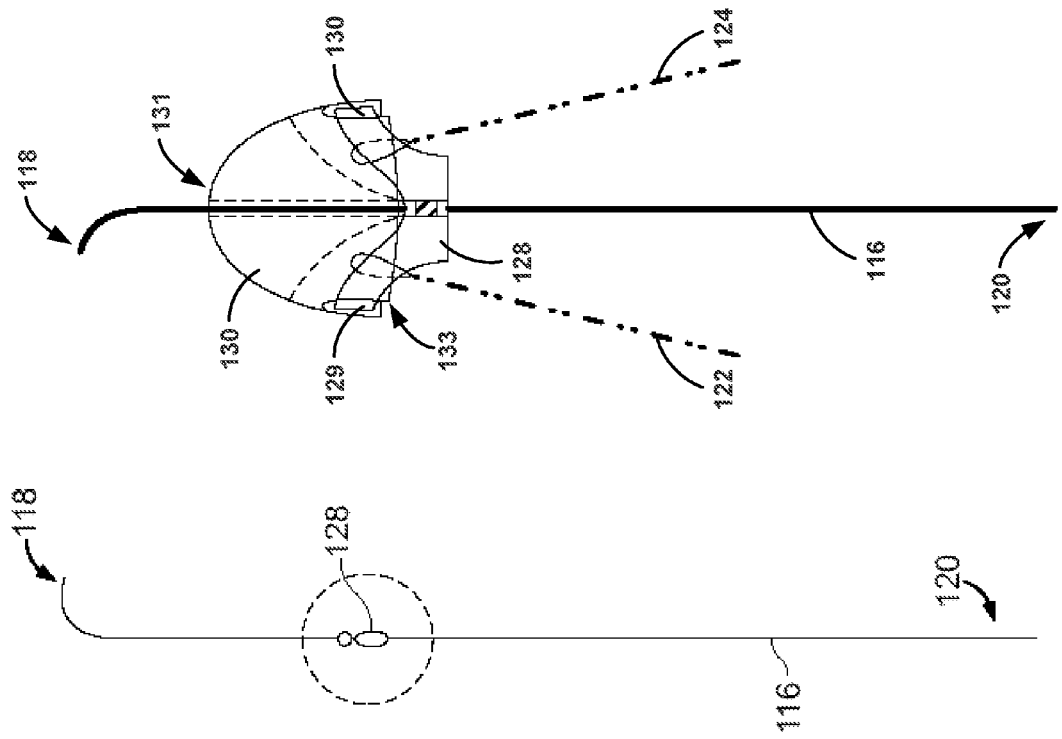
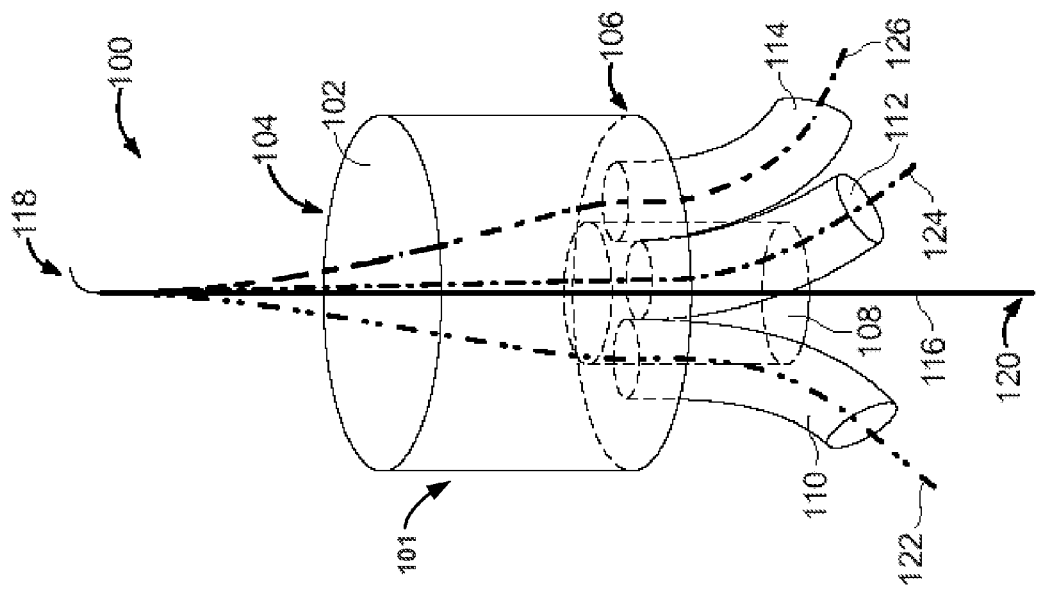
FIG. 3
FIG. 2
FIG. 1

GUIDE WIRE WITH MULTI-LUMEN ACCESS THREADS

RELATED APPLICATIONS

This application is a non-provisional of and claims priority to U.S. Provisional Application No. 62/127,257 entitled "Guidewire with Multi-Lumen Access Threads," filed on Mar. 2, 2015, which is hereby incorporated by reference in its entirety.

BACKGROUND OF THE INVENTION

Current stent graft devices with multiple openings or fenestrations require manual placement of wires into the various openings. With fenestrated stent grafts, both the main body stent graft and the bridging stents are typically delivered from a groin access. There are both advantages and disadvantages to such a configuration. For example, advantages may include only having to make two groin accesses instead of two groin accesses and an arm access such as is required for branch systems with antegrade flow characteristics. However, flow in fenestrated configurations may be turbulent and long term patency rates are typically low. Also, the case planning and procedure are often complex. Finally, such a device may require a long lead time because the device must be custom manufactured to match the specific anatomy of the patient.

To address the challenges of using fenestrated stent grafts, there are certain situations in which a cephalad access approach may be advantageous. For instance, this approach may allow the main body stent graft to be designed with antegrade flow to aid in long term patency. Cephalad access and antegrade flow also may allow the branch to be moved antegrade to the target vessel, which gives flexibility in graft placement. This addresses the shortcomings of fenestrated stent grafts where they require complex case planning, long customization lead times, and complex implant procedures.

Known antegrade branches have limitations. With side branches, an operator is required to select with a catheter and guide wire the opening of each branch along an inside wall of the main body stent graft. When advancing through a multi-lumen stent graft, the operator may be required to advance the guide wire and a directional catheter through a set of sequential bifurcations. If the operator is in the wrong branch of the stent graft, the directional catheter may be pulled back, turned and pointed toward the other branch, and re-advanced to the desired branch. In a stent graft in which the antegrade branch openings are at a common location at a single level in a plane it may be challenging to select the targeted branch. In such a configuration, operators may shoot nephrotoxic contrast dye into the openings of the stent graft to provide visibility of the various openings, which may increase radiation time of the patient and operator, and many times may not provide enough clarity to answer any clinical questions.

SUMMARY OF THE INVENTION

The speed and success of complicated aneurysm treatments may increase while lowering complications, in response to techniques and apparatus that increase the ease by which guide wires may be placed into individual branches or limbs of the stent graft or that eliminate the need to cannulate branch stents. The invention may beneficially predispose one or more alignment strings within the various branches of an implantable device (e.g., a stent graft) with multiple openings in order to decrease time to advance a delivery catheter to a target location in vivo. For example, after placement of a multi-lumen stent graft in a targeted location in vivo, one end of a guide wire may be captured with a tool, such as a snare, passing through a cephalad access point. Then the guide wire may be advanced through a patient's vasculature and exit the patient via the cephalad access point along with a portion of one or more alignment strings. The one or more alignment strings may then be disconnected from an affixing harness and used to advance one or more delivery catheters into a corresponding branch opening of the main body stent graft in which the respective alignment string is pre-disposed. The alignment strings may be replaced with guide wires once a delivery catheter is in place and may be used for improving the delivery of treatment devices such as bare metal stents, covered stents, and other over-the-wire devices.

Thus, in one aspect, the present disclosure provides an apparatus comprising (a) a guide wire having a first end and a second end, (b) an affixing harness coupled to the guide wire, the affixing harness having at least one projection extending towards the first end of the guide wire, (c) a plurality of alignment strings having a first end and a second end, where the first end of each of the plurality of alignment strings is removably coupled to the at least one projection of the affixing harness, and (d) an affixing shield removably coupled to at least one of the affixing harness and the guide wire, wherein the affixing shield is movably positioned over the at least one projection of the affixing harness.

In another aspect, the present disclosure provides an apparatus comprising (a) a stent graft having a main body including at least one lumen, wherein the main body has a first end and a second end, (b) a plurality of openings defined by at least one bifurcation in the at least one lumen of the main body of the stent graft, (c) a guide wire movably disposed through the main body and through a first opening of the plurality of openings such that a first end of the guide wire extends out of the first end of the main body and a second end of the guide wire extends beyond the first opening, (d) an affixing harness coupled to the guide wire, the affixing harness having at least one projection extending towards the first end of the guide wire, and (e) a plurality of alignment strings each having a first and a second end, wherein the first end of each of the plurality of alignment strings is removably coupled to the at least one projection of the affixing harness, and wherein each second end of the plurality of alignment strings is movably disposed through a different opening of the plurality of openings.

In yet another embodiment, the present disclosure provides a method for arterial placement of an apparatus. The method may include (a) introducing an apparatus of any of the embodiments described herein into an artery, (b) snaring the first end of the guide wire and pulling the guide wire and the affixing harness through an arterial access and advancing each of the plurality of alignment strings through a respective opening of a plurality of openings defined in a lumen of the main body stent graft such that the second end of each of the plurality of alignment strings extends beyond a second end of the main body stent graft, (c) uncoupling the first end of a first alignment string of the plurality of alignment strings from the affixing harness, (d) coupling the first end of the first alignment string to a locking wire partially disposed within a first delivery catheter, (e) pulling the locking wire and the alignment string into the delivery catheter containing a second stent graft, (f) moving the delivery catheter via the first alignment string and introducing the delivery catheter through a second opening of the plurality of openings of the main body of the stent graft, (g) advancing a second guide wire through the delivery catheter, and (h) deploying the second stent graft into at least one of the artery and the second opening of the plurality of openings of the main body of the stent graft.

BRIEF DESCRIPTION OF THE DRAWINGS

FIG. 1 is a perspective view of an apparatus disposed within a main body stent graft containing a diaphragm wherein all branch stents originate at the diaphragm, in accordance with one embodiment of the invention.

FIG. 2 is a front view of a guide wire, in accordance with one embodiment of the invention.

FIG. 3 is a side view of the apparatus, in accordance with one embodiment of the invention.

DETAILED DESCRIPTION OF THE INVENTION

Figure 4:
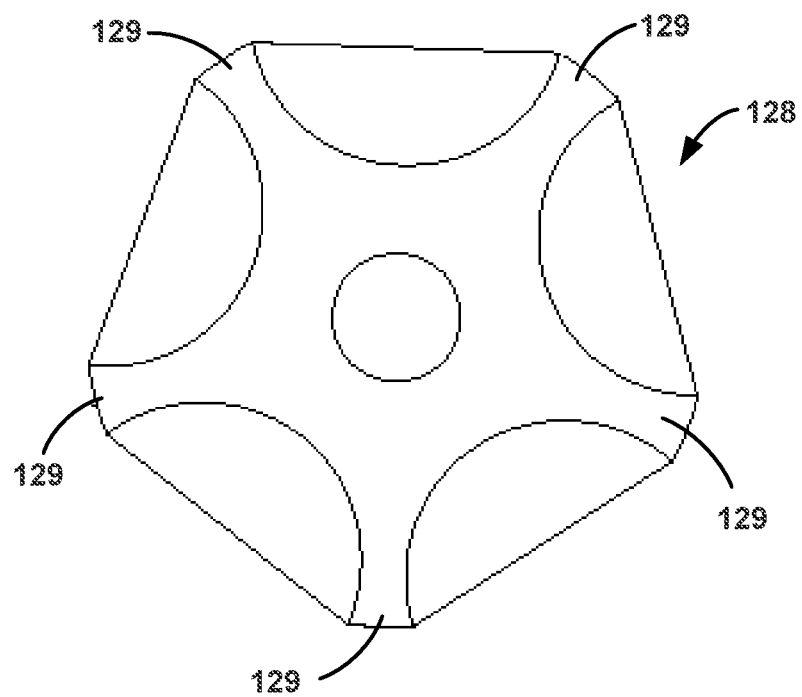
FIG. 4 is a top view of an affixing harness including a plurality of projections, in accordance with one embodiment of the invention.

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means +/−5%.

As used herein, "proximal" is defined as being closer to the heart, while "distal" is defined as being further from the heart.

As used herein, "cephalad" is defined as being near the head.

As used herein, "target branch arteries" are the arteries that originate at the aorta.

As used herein, a "stent graft" is a tubular, radially-expandable device comprising a fluid-tight fabric supported by a stent, and may be used to bridge aneurysmal arteries. As such, the term stent graft may be used herein to include bridging stent grafts. Such stent grafts and methods for their deployment and use are known to those of skill in the art. For example, vascular sheaths can be introduced into the patient's arteries, through which items, including but not limited to, guide wires, catheters and, eventually, the stent graft, is passed.

As used herein, "stent" is typically a cylindrical frame and means any device or structure that adds rigidity, expansion force, or support to a prosthesis, while "stent graft" refers to a prosthesis comprising a stent and a graft material associated therewith that forms a fluid-tight or blood-tight lumen through at least a portion of its length. A "graft" is a cylindrical liner that may be disposed on the stent's interior, exterior or both. A wide variety of attachment mechanisms are available to join the stent and graft together, including but not limited to, sutures, adhesive bonding, heat welding, and ultrasonic welding.

The stent can be made of any suitable material, including but not limited to biocompatible metals, implantable quality stainless steel wires, nickel and titanium alloys, and biocompatible plastics. The stents can either have material properties necessary to exhibit either self-expanding or balloon-expanding characteristics.

Any suitable fluid tight, or blood tight, graft material can be used. In a preferred embodiment, the graft material is a biocompatible fabric, including but not limited to woven or knitted polyester, such as poly(ethylene terephthalate), polylactide, polyglycolide and copolymers thereof; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. Materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. The graft material may also include extracellular matrix materials.

As used herein, a "common graft covering" refers to an uninterrupted continuous stent graft covering that extends from a single lumen or leg over at least one bifurcation and may overlap with another common graft covering. Stent grafts sewn together or built in a unitary fashion via weaving techniques, for example, may be used for complex aneurysm repair and may have a single main body lumen or bifurcated lumen. The single main body lumen may have side branches, a diaphragm defining openings coupled to tubular extension stent grafts, fenestrations or holes in the side wall of the main body, or sequential bifurcations, trifurcations, and quadrifications.

The stent graft components can be variously sized (i.e.: length, diameter, etc.) as suitable for an intended use, and are preferably larger in diameter than the inner vessel diameter to be treated. For example, aortic components may be oversized by approximately 10-20% of the diameter of the aorta or stent graft in which the stent graft is being deployed; limb components may be oversized by approximately 25% of the diameter of the target branch vessel or adjacent stent graft in which the stent graft is being deployed to increase fixation.

The stent grafts may contain any further suitable components, including but not limited to radiopaque markers to aid in visualization and to facilitate accurate placement of the stent graft. These radiopaque markers may take the form of gold bands at the distal end of each individual lumen of a given stent graft or a directional marker, for example in the shape of an "S" or any other suitable form for indicating direction and orientation of the stent graft. In addition, bi-directional anchoring hooks formed as part of the two most proximal individual stents of a given stent graft may be utilized to gain solid purchase and minimize the risk of stent graft migration in the non-diseased portion of a vessel wall also known as the seal zone. Further, a fixation stent may be located at the proximal end of a main body stent graft to permit radial force fixation within the vessel in conjunction with bidirectional hooks and to reduce the risk of stent graft migration.

As used herein, a "delivery catheter" is an apparatus that is connected to a deployment mechanism and houses a medical device that can be delivered over a guide wire. The delivery catheter may include a first end near a tip and a second end near a deployment handle. The delivery catheter may include a guide wire lumen for over-the-wire guidance and may be used for delivering stent graft to the aorta. The delivery catheter may also include radiopaque markers on the catheter which aid in radiographic placement. The delivery catheter may be deployed by pulling back the catheter with an actuator on the delivery system handle. The handle may remain outside of the patient and is the interface the physician uses for actuating the catheter portion.

As used herein, a "guide wire" is an elongated cable comprised of various biocompatible materials including metals and polymers. Guide wires may be used for selecting target lumens and guiding device delivery catheters to target deployment locations. Guide wires are typically defined as wires used independently of other devices that do not come as part of an assembly. In the present invention, guide wires may be used as a part of an assembly that, when used in conjunction, may facilitate several cannulations at once.

As used herein, a "cannulation" is the insertion of a cannula or tube into a hollow body organ or the lumen of a medical device which was previously placed within the artery of a patient.

As used herein, a "guide wire lumen" is defined as a space defined by a tubular surface structure, such as a guide wire housing, through which the guide wire or alignment strings are disposed.

As used herein, a "fluoroscope" is a type of medical imaging that shows a continuous x-ray image on a monitor, much like an x-ray movie. During a fluoroscope procedure, an x-ray beam is passed through the body to produce a radiographic image. The radiographic image is the image that the surgeon can see while performing the procedure mentioned herein which allows the surgeon to properly position and deploy the devices.

With reference to the Figures, FIG. 1 illustrates an example apparatus 100 according to one embodiment. As shown in FIG. 1, the apparatus includes a stent graft 101 with a main body 102 having a first end 104 and a second end 106. The apparatus 100 further includes a plurality of openings positioned at the second end 106 of the main body 102. In FIG. 1, more than one additional opening is shown. In particular, FIG. 1 illustrates a first opening 108, a second opening 110, a third opening 112 and a fourth opening 114. In other embodiments, there may be additional or fewer openings positioned at the second end 106 of the main body 102. In one embodiment, the plurality of openings are each defined by one or more bifurcations within the lumen of the main body 102 defined at the second end 106 of the main body 102 of the stent graft.

As shown in FIG. 1, the apparatus 100 further includes a guide wire 116 predisposed through the main body 102 and the first opening 108 such that a first end 118 of the guide wire 116 extends out of the first end 104 of the main body 102 and a second end 120 of the guide wire 116 extends out of the second end of the first opening 108. Further, the apparatus 100 includes a plurality of alignment strings 122, 124, and 126 predisposed through a respective opening of the plurality of openings 110, 112, and 114. The first end of each of the alignment strings 122, 124, and 126 extend beyond the first end 104 of the main body 102. The second end of each of the alignment strings 122, 124, and 126 extend beyond the second end of the corresponding opening 110, 112, and 114. In one example, the alignment strings 122, 124, and 126 may be non-resistant to compression or bending forces and resistant to tensile forces. In one particular example, the alignment strings 122, 124, and 126 may comprise a bio-compatible string, wire, or cable. As such, in one example the alignment strings 122, 124, and 126 may have a stiffness so as to enable the alignment strings 122, 124, and 126 to maintain their shape in both tension and compression.

Each of the alignment strings 122, 124, and 126 may have identifying marks such as colors and/or varying texture on the first end to differentiate between the plurality of alignment strings 122, 124, and 126. Such an indicator may be useful because the stent grafts may be designed so that each of the branch stents corresponds to a specific target branch artery. For example, determining where a given alignment string leads within the stent graft 101 is not always easy to determine on the radiographic image from the fluoroscope. So indicators on each alignment string 122, 124, and 126 can save time and protect from placing a stent graft in the wrong branch. For some designs, the stent grafts are built in such a way that the branches may be positioned to facilitate connection with a corresponding target branch vessel. As such, alignment of the branches with the correct corresponding target branch vessel is desired. Additionally, unique identifying markers on the alignment strings may enable a fixation harness with a single fixation point. This may be beneficial as it enables an embodiment wherein the profile or diameter of the catheter system can be reduced, hereby allowing for a smaller access hole in the vasculature thereby reducing access site complications in patients. A colorimetric identifier may be used by the physician in visually identifying the strings once the affixing harness has been pulled out of the arm access. In addition, a radiographic identifier could aid the physician in identifying the strings both when the affixing harness is inside or outside of the patient.

As shown in FIG. 2, the guide wire 116 includes a first end 118 and a second end 120. The first end 118 may be a snare end, and the second end 120 may be coupled to an affixing harness 128, as shown in FIG. 3. The first end 118 of the guide wire 116 may be straight, include an angled tip, or include a curved tip extending proximally from the affixing harness that can be snared from above. The first end 118 of the guide wire 116 may extend proximally in the patient and allow for ease of snaring from a cephalad access point, for example. The first end 118 of the guide wire 116 is the portion of the assembly that will be advanced proximally and through the cephalad access point.

The guide wire 116 may extend from the affixing harness 128 to the first end 118 of the guide wire 116. Alternatively, the guide wire 116 may extend from the first end 118 of the guide wire 116 past the affixing harness 128 and through one of the plurality of openings 108, 110, 112, 114 of the stent graft 101 and to the stent graft delivery system. The guide wire 116 may have sufficient compressive stiffness and kink resistance such that it may be either pushed or pulled from the first or second end through a given arterial configuration. Once the main body stent graft is deployed in the aorta, the second end 120 of the guide wire 116 can be manipulated by the user to push, pull, or turn the affixing harness 128 and first end 118 of the guide wire 116 beyond challenging vasculature facilitating snaring.

Figure 5:
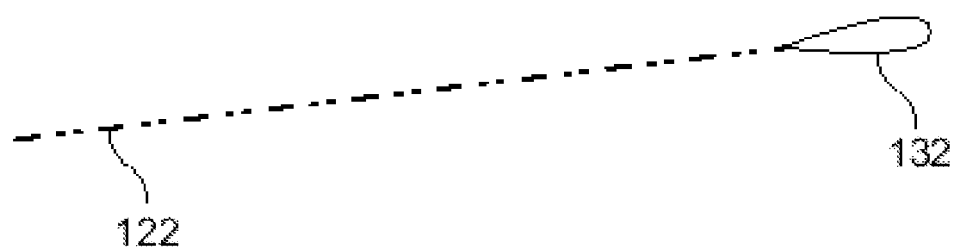
FIG. 5 is a side view of an alignment string, in accordance with one embodiment of the invention.

FIG. 3 illustrates the guide wire 116 coupled to the affixing harness 128. In one example, the affixing harness 128 may be permanently coupled to the guide wire 116. In another example, the affixing harness 128 may be removably coupled to the guide wire 116. In addition, as shown in FIG. 3, two alignment strings 122, 124 are shown removably coupled to the affixing harness 128. Although two alignment strings 122, 124 are shown in FIG. 3, there may be additional alignment strings removably coupled to the affixing harness 128 which may connect at multiple locations or a single location on the affixing harness 128. In one example, the affixing harness 128 is configured to have a plurality of locations to which the alignment strings 122, 124 can be temporarily or removably coupled. The affixing harness 128 can be made of any polymer, plastic, or metal material which is biocompatible and has a relatively high stiffness and structural stability. In one example, the affixing harness 128 may comprise at least one projection 129 extending in a direction toward the first end 118 of the guide wire 116. In one embodiment, the affixing harness 128 includes a plurality of projections 129 comprising a flexible plastic material that is capable of deforming or bending backwards in response to a force applied in the direction of the second end 120 of the guide wire 116. The deformation or bending of the plurality of projections 129 decouples the alignment strings 122, 124 from the affixing harness 128. Further, the plurality of projections 129 of the affixing harness 128 may comprise a shape memory material. Other examples are possible as well. The affixing harness 128 may include a number of different coupling mechanisms to removably couple the alignment strings 122, 124 to the guide wire 116. In one example, as shown in FIGS. 3, 4, 6, and 7, the affixing harness 128 may include a plurality of projections 129 extending towards the first end 118 of the guide wire 116. In such an example, the projections 129 may be arranged at an angle ranging from 0 degrees to 90 degrees with respect to the guide wire 116. Further, as shown in FIG. 5, the first ends of the alignment strings 122, 124 may include complementary loops 132 that may engage a corresponding projection 129 of the affixing harness 128.

Figure 8:
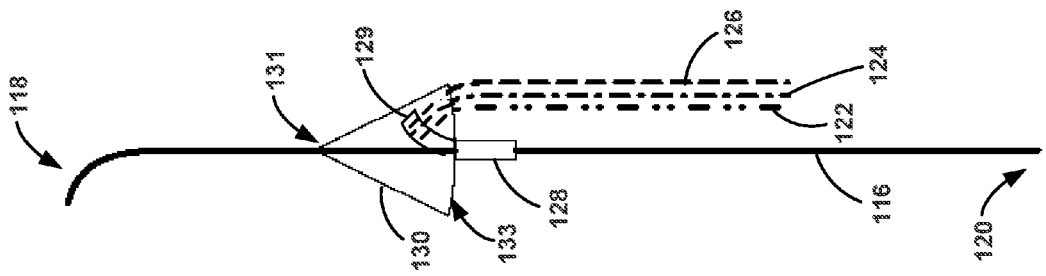
FIG. 8 is a side view of another example apparatus including an affixing harness with a single projection, in accordance with one embodiment of the invention.

In another example, as shown in FIG. 8, the affixing harness 128 may include a single projection 129 extending towards the first end 118 of the guide wire 116. In such an example, the first end of alignment strings 122, 124, and 126 may include complementary loops that may be removably coupled to the single projection 129.

In another example, the affixing harness 128 may include a clasp removably coupled to a hook or loop in the alignment string 122, 124. In another example, the affixing harness 128 may include a threaded female port, and the first end of each of the alignment strings 122, 124 may include a complementary threaded male locking member. In yet another example, the affixing harness 128 may include a first magnet, and the first end of each of the alignment strings 122, 124 may include a second magnet. Other example mechanisms are possible as well that form a force-resistant connection to resist the tension required to advance or pull the alignment string(s) to the desired location.

Further, the apparatus may include an affixing shield 130 positioned over the first end of the alignment strings 122, 124. The affixing shield 130 is a removable wire mounted device that when in place aids in securing the alignment strings 122, 128 to the affixing harness 128, and once removed allows the alignment strings 122, 128 to be separated from the affixing harness 128. In one example, the affixing shield 130 is removably coupled to the guide wire 116. In another example, the affixing shield 130 is removably coupled to the affixing harness 128. In such an example, as shown in FIG. 3, the affixing shield 130 may include a male threaded locking member and the affixing harness 128 may include a complementary female threaded locking member. Other coupling mechanisms are possible as well. The affixing shield 130 may be made of any biocompatible polymer, plastic, or metal material. In one example, the affixing shield 130 is flexible and has shape memory. In another example, the affixing shield 130 is rigid, and does not have shape memory. As shown in FIGS. 3 and 8, the affixing shield 130 has a first end 131 and a second end 133. In one example, the first end 131 of the affixing shield 130 is tapered or rounded, and the second end 133 of the affixing shield 130 covers the projection(s) 129 of the affixing harness 128. In one example, the affixing shield 130 has a conical shape with a narrow section at the first end 131 of the affixing shield 130 and the base of the cone at the second end 133 of the affixing shield 130.

Figure 7:
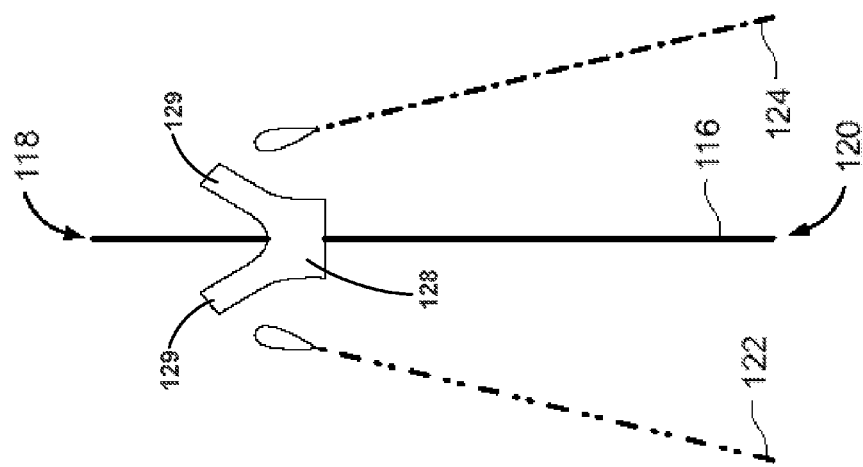
FIG. 7 is a side view of the apparatus with the alignment strings decoupled from the affixing harness, in accordance with one embodiment of the invention.
Figure 6:
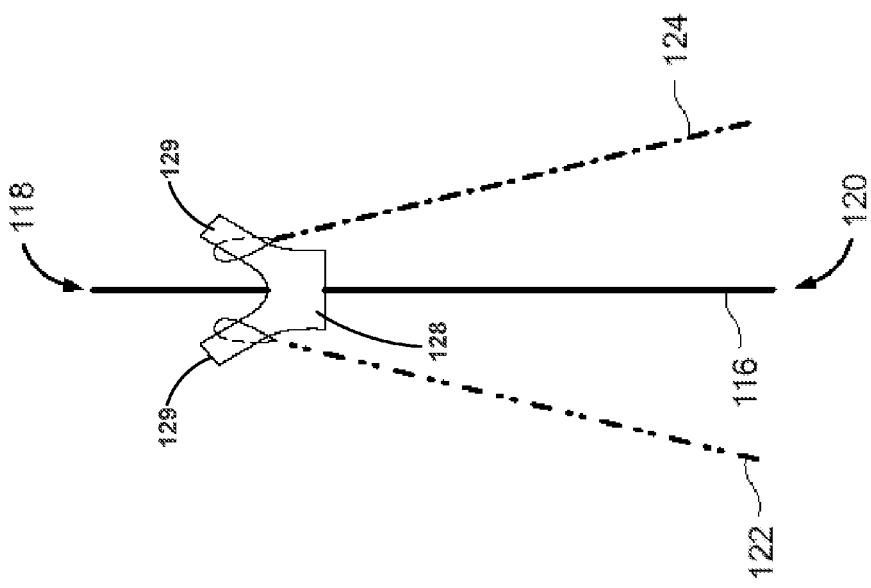
FIG. 6 is a side view of the apparatus with the alignment strings each removably coupled to one of the plurality of projections of the affixing harness, in accordance with one embodiment of the invention.

In one example, the affixing shield 130 has a sized to receive and cover the projections 129 of the affixing harness 128 in a deployment position. In such a deployment position, the affixing shield 130 allows for a smooth transition over the affixing harness 128 such that the affixing harness 128 does not accidentally snag arterial or device structures when the apparatus is in use. This has the benefit of reducing the chance of the affixing harness 128 snagging a component of the stent graft, which may dislodge or damage the stent graft, dislodge an embolus, or damage the artery. In such an example, the affixing harness 128 may even become permanently snagged requiring an open surgical repair to dislodge, dramatically increasing the patient's risk. The affixing shield 130 can also block or deflect the projections 129 of the affixing harness 128 from contacting any stent graft or arterial structures when it is pulled through the arm access. Once the affixing shield 130 is removed, as shown in FIGS. 6 and 7, it will allow the removal of alignment strings 122, 124 from the affixing harness 128.

FIG. 5 illustrates a first end of an alignment string 122 including a loop 132, as discussed above. As discussed above, the loop 132 on the alignment string 122 allows for separation from the affixing harness 128 of the guide wire 116. In addition, the loop 132 on the alignment string 122 allows for temporary connection with a locking wire 134 over which a stent graft delivery catheter 136 can pass.

Figure 9:
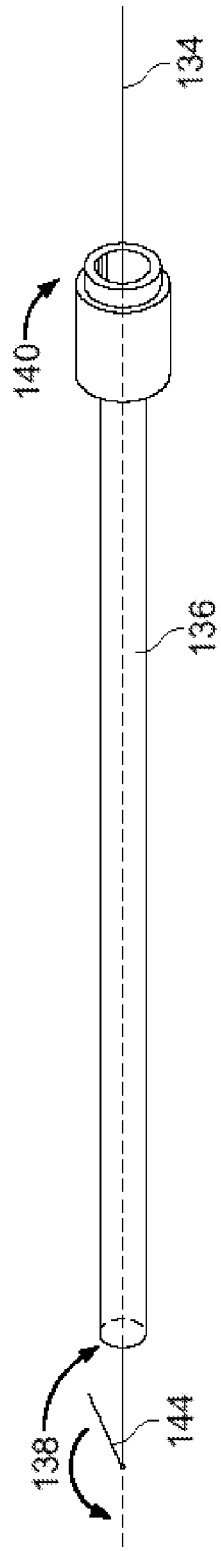
FIG. 9 is a side view of a delivery catheter in a first position, in accordance with one embodiment of the invention.
Figure 10:
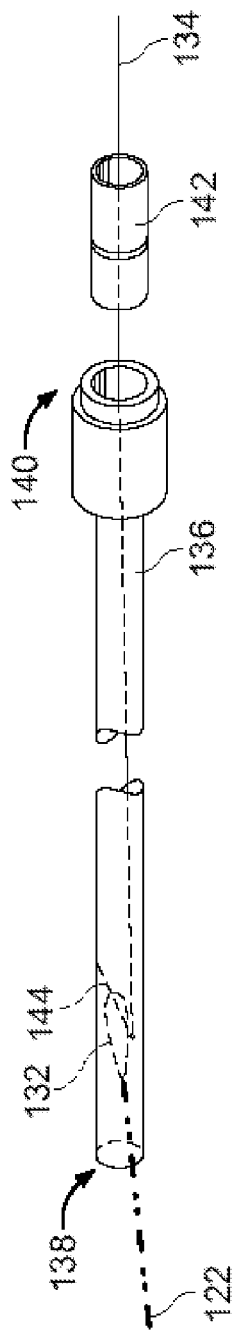
FIG. 10 is a side view of a delivery catheter in a second position, in accordance with one embodiment of the invention.
Figure 11:
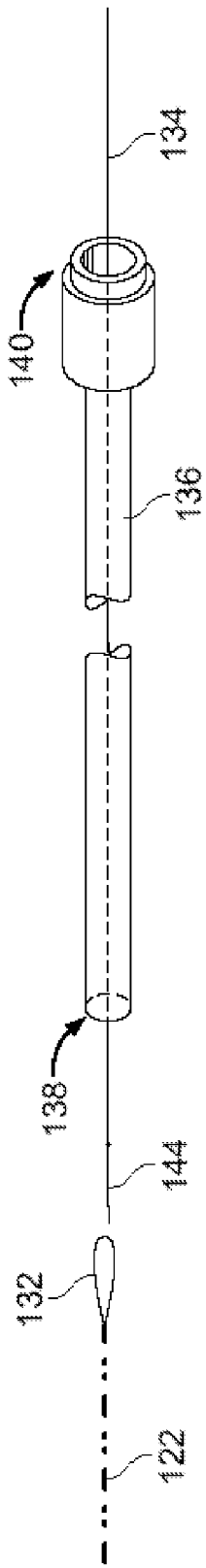
FIG. 11 is a side view of a delivery catheter in a third position, in accordance with one embodiment of the invention.

Such a stent graft delivery catheter 136 is shown in various stages of operation in FIGS. 9-11. As shown in FIGS. 9-11, the delivery catheter 136 has a first end 138 and a second end 140. The delivery catheter 136 may be any commercially available catheter. In one embodiment, the locking wire 134 may be passed into the delivery catheter 136 and locked into place using a torque lock 142 on the locking wire 134. In one example, the torque lock may be positioned adjacent to the second end 140 of the delivery catheter 136. In another example, the torque lock may be coupled to the second end 140 of the delivery catheter 136. The torque lock 142 may comprise a small cylindrical apparatus that is made of polymers and that can be advanced over the first end 138 of the locking wire 134 until adjacent to the delivery catheter handle. When torqued, the torque lock 142 squeezes the locking wire 134 effectively preventing the stent graft delivery catheter 136 from sliding over the first end of the locking wire 134. With the locking wire 134 extending beyond the first end 138 of the delivery catheter 136 as shown in FIG. 9, the locking wire 134 can engage the loop 132 on the first end of the alignment string 122.

In a first position, as shown in FIGS. 3 and 8, the plurality of alignment strings 122, 124 are removably coupled to the affixing harness 128. In a second position, at least one of the plurality of alignment strings 122, 124 may be decoupled from the affixing harness 128 and removably coupled to the locking wire 134. The at least one alignment string 122 and the locking wire 134 can be removably coupled through a number of temporary coupling mechanisms. For example, the locking wire 134 may include a threaded female connector, a first magnet, or a locking hinge and the alignment string 122 may then include a corresponding male connector, a second magnet, or a loop on the alignment string 122. A hinge tip 144 and corresponding loop 132 in the alignment string 122 is illustrated in FIGS. 9-11. Once the alignment string 122 is coupled to the locking wire 134, the torque lock 142 may be unlocked and the locking wire 134 may be advanced toward the second end 140 of the delivery catheter 136 effectively pulling the proximal affixing end through the delivery catheter tip. From here the delivery catheter 136 can be advanced over the alignment string 122, through the branch lumen by pulling on the alignment string 122 from the groin access, thereby facilitating the movement of the delivery catheter through the lumen of the branch stent. Then the hinge tip 144 can be released on the locking wire 134 as shown in FIG. 11, the alignment string 122 removed from the patient, and the locking wire 134 can be removed from the patient. The locking wire 134 can then be replaced with a normal guide wire for the purpose of selecting and cannulating the target vessel.

Figure 12:
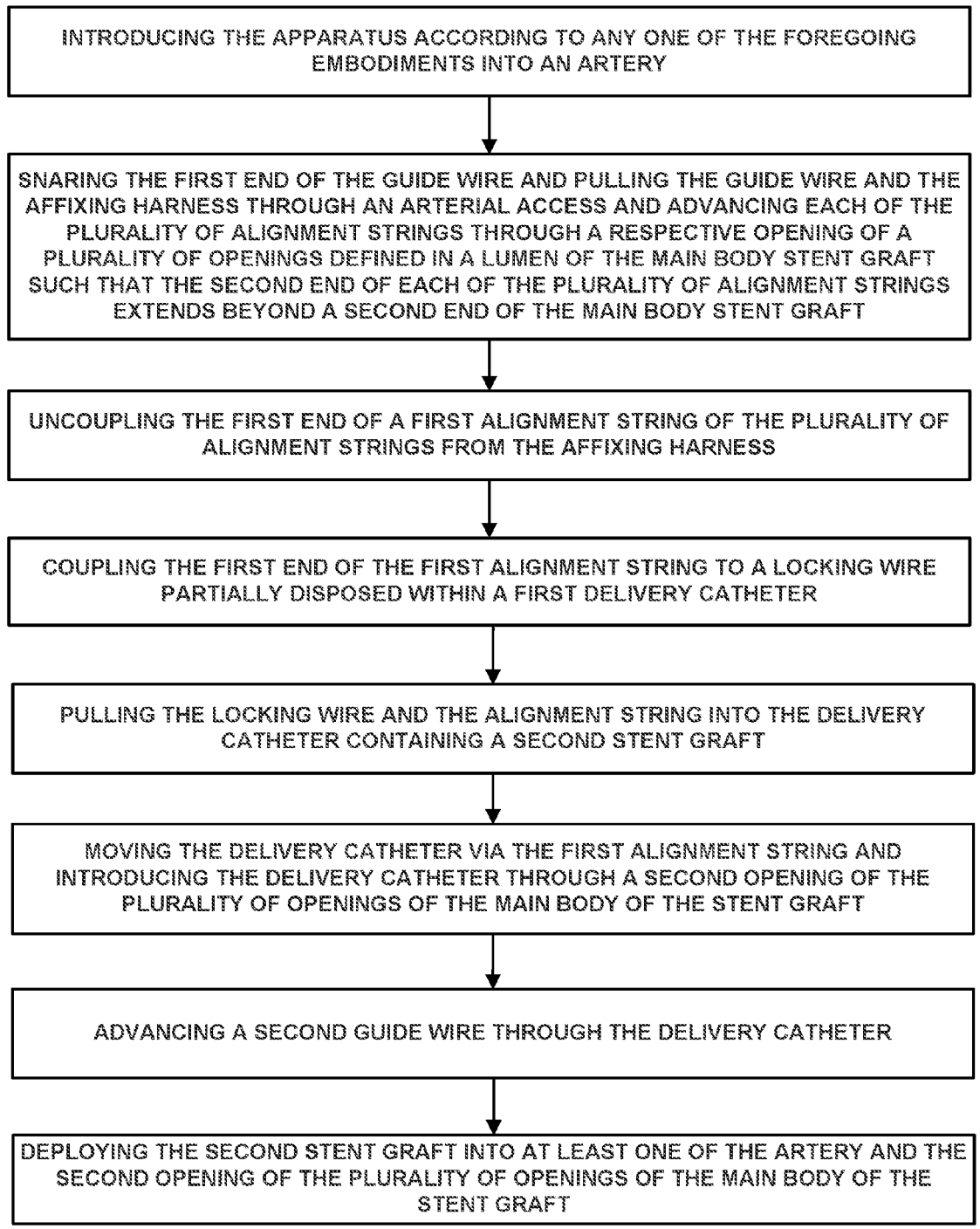
FIG. 12 is a flow chart depicting functions that can be carried out in accordance with example embodiments of the disclosed methods.

FIG. 12 is a simplified flow chart illustrating a method according to an exemplary embodiment. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

One example method for placement of an apparatus having a plurality of openings comprises (a) introducing the apparatus according to any one of the foregoing embodiments into an artery, (b) snaring the first end of the guide wire and pulling the guide wire and the affixing harness through an arterial access and advancing each of the plurality of alignment strings through a respective opening of a plurality of openings defined in a lumen of the main body stent graft such that the second end of each of the plurality of alignment strings extends beyond a second end of the main body stent graft, (c) uncoupling the first end of a first alignment string of the plurality of alignment strings from the affixing harness, (d) coupling the first end of the first alignment string to a locking wire partially disposed within a first delivery catheter, (e) pulling the locking wire and the alignment string into the delivery catheter containing a second stent graft, (f) moving the delivery catheter via the first alignment string and introducing the delivery catheter through a second opening of the plurality of openings of the main body of the stent graft, (g) advancing a second guide wire into the delivery catheter, and (h) deploying the second stent graft into at least one of the artery and the second opening of the plurality of openings of the main body of the stent graft.

In particular, the first end of the first alignment string may be coupled to a hinge tip of the locking wire disposed within the delivery catheter. The method may then include pulling the locking wire and alignment string into the delivery catheter, so as to affix the hinge tip and alignment string loop in the delivery catheter tip. The method may then include pulling the alignment string from the groin access until the delivery catheter is disposed within a branch lumen, uncoupling the locking wire from the alignment string, exchanging and advancing a wire into the delivery catheter and securing access to the artery, and deploying the stent graft into at least one of the target branch artery and the second opening.

In another embodiment, the method may further comprise (i) uncoupling a first end of a second alignment string of the plurality of alignment strings from the affixing harness, (j) removably coupling the first end of the second alignment string to a second locking wire partially disposed within a second delivery catheter, (k) pulling the second locking wire and second alignment string into the second delivery catheter containing a third stent graft, (l) moving the second delivery catheter via the second alignment string and introducing the second delivery catheter into a third opening of the plurality of openings of the main body of the stent graft, (m) advancing a third guide wire through the second delivery catheter, and (n) deploying the third stent graft into at least one of the artery and the third opening of the main body of the stent graft.

In particular, the first end of the second alignment string may be coupled to a hinge tip of the locking wire partially disposed within a second delivery catheter. The method may then include pulling the second alignment string loop and locking wire hinge tip into the second delivery catheter tip, placing a torque lock on the locking wire adjacent to the second end of the second delivery catheter, pulling the alignment string from the groin access until the second delivery catheter is partially disposed in a branch stent lumen, uncoupling the locking wire and second alignment string, exchanging the locking wire for a guide wire, selecting the second target branch vessel, advancing the stent graft under fluoroscopic guidance and deploying the stent graft between the target branch vessel and branch stent.

The target branch arteries may be arteries that originate at the aorta. As such, the methods described herein may be used in cannulating the openings of branch stent grafts, in particular for cannulating the openings of branch stent grafts when repairing aneurysms of the branched visceral segment of the aorta. In such an example, the important branch arteries are the celiac artery, the superior mesenteric artery, the left renal artery, and the right renal artery. Other important branch arteries include those of the arch: the innominate artery, left common carotid artery, and left subclavian artery as well as the branches of the iliac artery including the external iliac artery and internal iliac artery. Other target branch arteries are possible as well.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the following claims.

The invention claimed is:

1. An apparatus, comprising:
    a guide wire having a first end and a second end;
    an affixing harness coupled to the guide wire, the affixing harness having at least one projection extending towards the first end of the guide wire;
    a plurality of alignment strings having a first end and a second end, wherein the first end of each of the plurality of alignment strings is removably coupled to the at least one projection of the affixing harness; and
    an affixing shield removably coupled to at least one of the affixing harness and the guide wire, wherein the affixing shield is movably positioned over the at least one projection of the affixing harness, and wherein the affixing shield is flexible and has shape memory.

2. The apparatus of claim 1, wherein the affixing harness is removably coupled to the guide wire.

3. The apparatus of claim 2, wherein the first end of each of the plurality of alignment strings includes a loop removably coupled to a corresponding projection of the affixing harness.

4. The apparatus of claim 1, wherein the at least one projection of the affixing harness comprises a plurality of projections extending towards the first end of the guide wire.

5. The apparatus of claim 1, wherein the at least one projection of the affixing harness comprises a single projection extending towards the first end of the guide wire.

6. The apparatus of claim 5, wherein the first end of each of the plurality of alignment strings includes a loop removably coupled to the single projection of the affixing harness.

7. The apparatus of claim 1, wherein the affixing shield has a first end and a second end, wherein the first end of the affixing shield is tapered, and wherein the affixing shield has a cavity configured to receive the at least one projection of the affixing harness.

8. The apparatus of claim 1, wherein the affixing shield is conical.

9. The apparatus of claim 1, wherein the plurality of alignment strings are removably coupled to the affixing harness in a first position, the apparatus further comprising:
    a delivery catheter; and
    a locking wire partially disposed within the delivery catheter, wherein the locking wire includes a coupling mechanism comprising a threaded female connector, a first magnet, or a locking hinge and the plurality of alignment strings each include a corresponding male connector, a second magnet, or a loop, wherein at least one of the plurality of alignments strings is decoupled from the affixing harness and removably coupled to the locking wire in a second position.

10. The apparatus of claim 9, further comprising:
    a torque lock positioned adjacent to the delivery catheter, wherein the torque lock is configured to prevent the delivery catheter from moving with respect to the locking wire in a locked mode, and wherein the torque lock is configured to allow the delivery catheter to move along the locking wire in an unlocked mode.

11. The apparatus of claim 9, further comprising:
    a torque lock coupled to the second end of the delivery catheter, wherein the torque lock is configured to prevent the delivery catheter from moving with respect to the locking wire in a locked mode, and wherein the torque lock is configured to allow the delivery catheter to move along the locking wire in an unlocked mode.

12. The apparatus of claim 1, wherein the at least one projection of the affixing harness is deformable with respect to a force applied in the direction of the second end of the guide wire.

13. The apparatus of claim 1, wherein in a deployment position of the affixing shield, the affixing shield is arranged surrounding the at least one projection of the affixing harness.

14. An apparatus, comprising:
    a stent graft having a main body including at least one lumen, wherein the main body has a first end and a second end;
    a plurality of openings defined by at least one bifurcation in the at least one lumen of the main body of the stent graft;
    a guide wire movably disposed through the main body and through a first opening of the plurality of openings such that a first end of the guide wire extends out of the first end of the main body and a second end of the guide wire extends beyond the first opening;
    an affixing harness coupled to the guide wire, the affixing harness having at least one projection extending towards the first end of the guide wire; and
    a plurality of alignment strings each having a first and a second end, wherein the first end of each of the plurality of alignment strings is removably coupled to the at least one projection of the affixing harness, and wherein each second end of the plurality of alignment strings is movably disposed through a different opening of the plurality of openings.

15. The apparatus of claim 14, further comprising:
    an affixing shield removably coupled to at least one of the affixing harness and the guide wire, wherein the affixing shield is movably positioned over the at least one projection of the affixing harness.

16. The apparatus of claim 15, wherein the affixing shield has a first end and a second end, wherein the first end of the affixing shield is tapered, and wherein the second end of the affixing shield covers the at least one projection of the affixing harness.

17. The apparatus of claim 15, wherein in a deployment position the affixing shield is arranged surrounding the at least one projection of the affixing harness.

18. The apparatus of claim 14 wherein the affixing harness includes a plurality of projections extending towards the first end of the guide wire.

19. The apparatus of claim 18, wherein the first end of each of the plurality of alignment strings includes a loop removably coupled to a corresponding projection of the affixing harness.

20. The apparatus of claim 14, wherein the affixing harness includes a single projection extending towards the first end of the guide wire.

21. The apparatus of claim 20, wherein the first end of each of the plurality of alignment strings includes a loop removably coupled to the single projection of the affixing harness.

22. The apparatus of claim 14, wherein the affixing shield has a first end and a second end, wherein the first end of the affixing shield is tapered, and wherein the second end of the affixing shield covers the at least one projection of the affixing harness.

23. The apparatus of claim 14, wherein the plurality of alignment strings are removably coupled to the affixing harness in a first position, the apparatus further comprising:
 a delivery catheter; and
 a locking wire partially disposed within the delivery catheter, wherein the locking wire includes a coupling mechanism comprising a threaded female connector, a first magnet, or a locking hinge and the plurality of alignment strings each include a corresponding male connector, a second magnet, or a loop, wherein at least one of the plurality of alignment strings is decoupled from the affixing harness and removably coupled to the locking wire in a second position.

24. The apparatus of claim 23, further comprising:
a torque lock positioned adjacent to the delivery catheter, wherein the torque lock is configured to prevent the delivery catheter from moving with respect to the locking wire in a locked mode, and wherein the torque lock is configured to allow the delivery catheter to move along the locking wire in an unlocked mode.

25. The apparatus of claim 23, further comprising:
a torque lock coupled to the second end of the delivery catheter, wherein the torque lock is configured to prevent the delivery catheter from moving with respect to the locking wire in a locked mode, and wherein the torque lock is configured to allow the delivery catheter to move along the locking wire in an unlocked mode.

26. The apparatus of claim 23, further comprising:
a torque lock disposed along the guide wire and positioned adjacent to the delivery catheter, wherein the torque lock is configured to prevent the delivery catheter from moving with respect to the locking wire in a locked mode, and wherein the torque lock is configured to allow the delivery catheter to move along the locking wire in an unlocked mode.

27. The apparatus of claim 14, wherein the at least one projection of the affixing harness is deformable in response to a force applied via one of the plurality of alignment strings.

28. A method comprising:
introducing the apparatus of claim 1 into an artery;
snaring a first end of the guide wire and pulling the guide wire and the affixing harness through an arterial access and advancing each of the plurality of alignment strings through a respective opening of the plurality of openings defined in a lumen of a main body stent graft such that a second end of each of the plurality of alignment strings extends beyond a second end of the main body stent graft;
snaring a first end of the guide wire and pulling the guide wire and the affixing harness through an arterial access and advancing each of the plurality of alignment strings through a respective opening of a plurality of openings defined in a lumen of a main body stent graft such that the second end of each of the plurality of alignment strings extends beyond a second end of the main body stent graft;
uncoupling the first end of a first alignment string of the plurality of alignment strings from the affixing harness;
coupling the first end of the first alignment string to a locking wire partially disposed within a first delivery catheter;
pulling the locking wire and the alignment string into the delivery catheter containing a second stent graft;
moving the delivery catheter via the first alignment string and introducing the delivery catheter through a second opening of the plurality of openings of the main body of the stent graft;
advancing a second guide wire through the delivery catheter and securing access to the artery; and
deploying the second stent graft into at least one of the artery and the second opening of the plurality of openings of the main body of the stent graft.

29. The method of claim 28, further comprising:
uncoupling a first end of a second alignment string of the plurality of alignment strings from the affixing harness;
removably coupling the first end of the second alignment string to a second locking wire partially disposed within a second delivery catheter;
pulling the second locking wire and second alignment string into the second delivery catheter containing a third stent graft;
moving the second delivery catheter via the second alignment string and introducing the second delivery catheter into a third opening of the plurality of openings of the main body of the stent graft;
advancing a third guide wire through the second delivery catheter; and
deploying the third stent graft into at least one of the artery and the third opening of the main body of the stent graft.

\* \* \* \* \*